United States Patent [19]

Levin

[11] Patent Number: 5,852,213

[45] Date of Patent: Dec. 22, 1998

[54] MERCAPTOKETONES AND MERCAPTOALCOHOLS AND A PROCESS FOR THEIR PREPARATION

[75] Inventor: Jeremy Ian Levin, Nannet, N.Y.

[73] Assignee: American Cyanamid Company, Madison, N.J.

[21] Appl. No.: 887,000

[22] Filed: Jul. 2, 1997

Related U.S. Application Data

[60] Provisional application No. 60/022,469, Jul. 10, 1996.

[51] Int. Cl.$^6$ .................. C07C 321/12; C07C 231/02
[52] U.S. Cl. .................. 564/154; 544/335; 546/164; 546/165; 546/175; 546/329; 548/304.4; 548/309.7; 548/336.1; 548/491; 549/58; 549/76; 549/467; 549/496; 549/483; 549/488; 558/436; 560/147; 562/581; 564/138; 564/139
[58] Field of Search .................. 564/138, 139, 564/154; 549/483, 488, 58, 76, 467, 496; 544/335; 546/164, 165, 175, 329, 304.4, 309.7, 336.1, 491; 558/436; 560/147; 562/581

[56] References Cited

U.S. PATENT DOCUMENTS

| 4,595,700 | 6/1986 | Donald | 514/616 |
| 4,599,361 | 7/1986 | Dickens | 514/575 |

FOREIGN PATENT DOCUMENTS

| 0322184 | 6/1989 | European Pat. Off. | C07C 149/23 |
| WO9425435 | 11/1904 | WIPO . | |
| 9407481 | 4/1994 | WIPO | A61K 31/16 |
| 9509620 | 4/1995 | WIPO | A61K 31/16 |
| 9509833 | 4/1995 | WIPO | C07C 233/03 |
| 9513289 | 5/1995 | WIPO | C07K 5/062 |
| 9640204 | 12/1996 | WIPO | A61K 38/05 |
| 9640738 | 12/1996 | WIPO | C07K 5/00 |

OTHER PUBLICATIONS

Guillerm et al, Tetrahedron Letters, vol. 33, No. 35, pp. 5047–5050, 1992.
Morphy et al., Current Medicinal Chemistry, 1995, 2, 743–762.
Bezant et al., J. Med. Chem. 1993, vol. 36, 4030–4039.
Beeley et al., Curr. Opin. Ther. Patents(1994) $(1):7–16.
Hodgson, Bio/Technology vol. 13, 554–557, 1995.

*Primary Examiner*—Shailendra Kumar
*Attorney, Agent, or Firm*—Rebecca R. Barrett

[57] ABSTRACT

This invention relates to matrix metalloproteinase (MMP) inhibiting compounds of the formula:

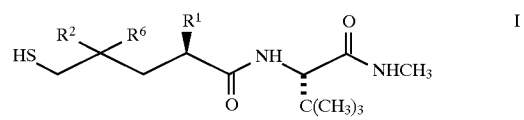

where $R^1$ is $C_1$–$C_{12}$ alkyl, straight or branched and optionally substituted by halogen, hydroxy, $C_1$–$C_6$ alkoxy, amino, carboxyl, $C_1$–$C_6$ alkoxycarbonyl, carboxamido, nitrile, mono- or di-($C_1$–$C_6$)alkylamino, thio, $C_1$–$C_6$ alkylthio, aryl, —Oaryl or —OCH$_2$aryl where aryl is optionally substituted with $C_1$–$C_6$ alkyl, $C_1$–$C_6$ alkoxy, carboxy, halogen, cyano, nitro, carboxamido, or hydroxy; and $C_1$–$C_6$ alkanesulfonyloxy. $R^2$ is α-OH or β-OH and $R^6$ is H or $R^2$ and $R^6$ together are carbonyl; the chemical intermediates; and processes for the preparation of these compounds and the intermediates thereto.

Matrix metalloproteinases (MMP) are a family of zinc-containing calcium dependent proteinases, including stromelysins, collagenases, and gelatinases. These MMP enzymes are capable of degrading the proteinaceous components of connective tissue and appear to be involved in tissue remodeling, i.e., wound healing and connective tissue turnover. Unexpectedly, the mercaptoalcohols with the S-configuration at the hydroxyl-bearing carbon have been found to be at least 4 times more potent than the analogous (R)-alcohols both in vitro and in vivo in inhibiting the MMP enzyme.

4 Claims, No Drawings

MERCAPTOKETONES AND MERCAPTOALCOHOLS AND A PROCESS FOR THEIR PREPARATION

This application claims priority to the provisional patent application number 60/022,469 filed on Jul. 10, 1996.

FIELD OF INVENTION

This invention relates to mercaptoketone and diastereomeric mercaptoalcohol derivatives of Formula I useful as matrix metalloproteinase inhibitors and a process for the stereospecific synthesis of each of the diasteromers. Unexpectedly, the mercaptoalcohols with the S-configuration at the hydroxyl-bearing carbon have been found to be at least 4 times more potent than the analogous (R)-alcohols both in vitro and in vivo.

BACKGROUND OF THE INVENTION

Matrix metalloproteinases (MMP) are a family of zinc-containing calcium dependent proteinases, including stromelysins, collagenases, and gelatinases. These MMP enzymes are capable of degrading the proteinaceous components of connective tissue and appear to be involved in tissue remodeling, i.e., wound healing and connective tissue turnover. Approximately thirteen MMPs have been identified. The collagenases cleave fibrillar collagen. The stromelysins degrade fibronectin, laminin, and proteoglycans in addition to collagen. The gelatinases can degrade denatured collagen (gelatin) and type IV collagen, the major component of basement membranes.

Elevated levels of collagenase and stromelysin are associated with both osteo- and rheumatoid arthritis, having been observed both in synovium and cartilage in amounts proportional to the severity of the disease. The gelatinases are thought to play a key role in tumor metastasis, since they degrade the basement membrane through which tumor cells must pass in order to migrate away from the primary tumor site and thus enable the migration from the primary site. Gelatinase is also associated with the process of angiogenesis which is essential for the growth of solid tumors. In addition to the association with osteo- and rheumatoid arthritis and tumor metastasis, MMPs are implicated in corneal ulceration, gingivitis, multiple sclerosis and other neurological disorders, and emphysema (Beeley et al., *Curr. Opin. Ther. Patents* 4(1), 7–16 (1994)).

Compounds which bind zinc at the active site of the enzyme prevent the catalytic activity of MMPs. MMP inhibitor activity has been found in certain peptidyl hydroxamic acids, peptidylalkyl carboxylic acids, peptidylphosphinic and phosphonic acids. Furthermore, peptidyl thiols incorporating a carbonyl group two atoms removed from the thiol group have been shown to be potent MMP inhibitors. For example, in the compound below, as disclosed in *Journal of Medicinal Chemistry* 36, 4030–4039 (1993), the SSR

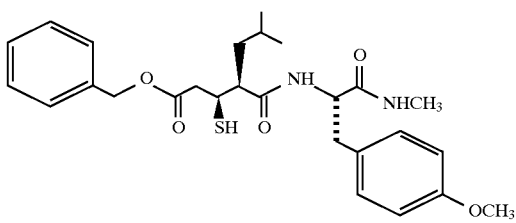

isomer is a potent ($IC_{50}$=2 nM) inhibitor of human collagenase (J. R. Morphy et al., *Current Medicinal Chemistry* 2, 743–762 (1995)).

Merck discloses the compound

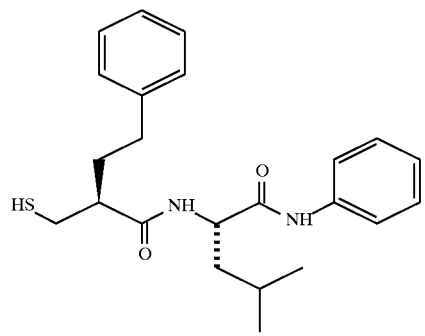

in the PCT application WO 9407481 as a moderate inhibitor of the MMP stromelysin. The compound

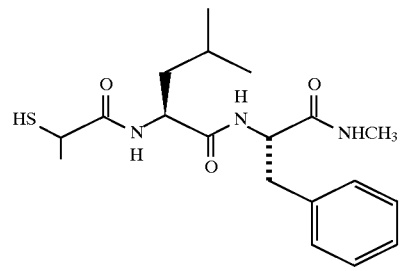

is disclosed in the PCT application WO 9513289. The mercapto sulfide MMP inhibitor compound below was disclosed in the PCT application WO 9509833.

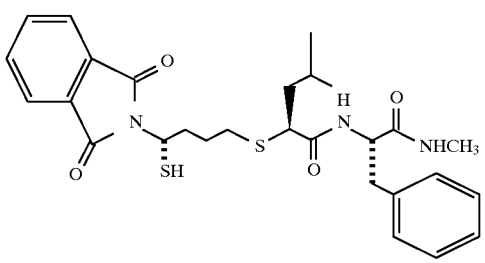

MMP inhibiting compounds of the formula

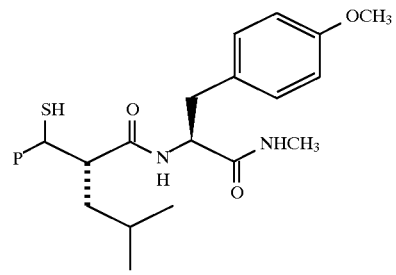

where P is H, methyl or phenyl are disclosed by Donald et al., U.S. Pat. No. 4,595,700. The compound where P is 2-oxopropyl is approximately 20 times more potent than the compound where P is methyl which is in turn about 20 times more potent than the compound where P is hydrogen (EP 0322,184 A2). In all of the above noted examples the thiol moiety is two carbons removed from an amide carbonyl group.

BRIEF DESCRIPTION OF THE INVENTION

The matrix metalloproteinase inhibiting compounds of this invention are represented by formula I

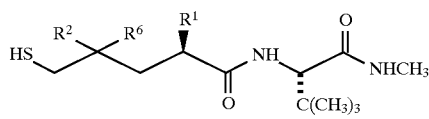

where $R^1$ is $C_1$–$C_{12}$ alkyl, straight or branched and optionally substituted by halogen, hydroxy, $C_1$–$C_6$ alkoxy, amino, carboxyl, $C_1$–$C_6$ alkoxycarbonyl, carboxamido, nitrile, mono- or di-($C_1$–$C_6$)alkylamino, thio, $C_1$–$C_6$ alkylthio, aryl, —Oaryl or —OCH$_2$aryl where aryl is optionally substituted with $C_1$–$C_6$ alkyl, $C_1$–$C_6$ alkoxy, carboxy, halogen, cyano, nitro, carboxamido, or hydroxy; and $C_1$–$C_6$ alkanesulfonyloxy. $R^2$ is α-OH or β-OH and $R^6$ is H or $R^2$ and $R^6$ together forms carbonyl. In the above definition, aryl is a 5 to 10 membered carbocyclic or heterocyclic mono or bicyclic aromatic group such as benzene, furan, thiophene, imidazole, naphthalene, quinoline, indole, benzothiophene, benzimidazole, pyridine, pyrimidine or benzofuran. This invention also encompasses all of the chemical intermediates required for the synthesis of compounds of formula I.

The diastereomeric compounds of formula I have been shown to inhibit the matrix metalloproteinases collagenase, stromelysin and gelatinase, both in vitro and in vivo and are thus expected to be useful in the treatment of arthritis, corneal ulceration, multiple sclerosis, gingivitis, emphysema, inhibition of solid tumor growth, and prevention of tumor metastasis. The stereospecific synthesis of the mercaptoalcohols is desirable since the alcohols of the (S)-configuration (formula I, $R^2$ is β-OH) have been found to be at least 4 times more potent than the corresponding (R)-configured diastereomers both in vitro and in vivo. Disclosed herein is a process by which either of the two diastereomers of compounds of formula I ($R^2$ is α-OH or β-OH) can be synthesized via intermediate lactone diastereomers. Also disclosed herein are diastereomerically and entaniomerically pure intermediates and processes for their preparation.

DETAILED DESCRIPTION OF THE INVENTION

The process for the sterospecific synthesis of each of the diastereomeric alcohols and ketones of Formula I is shown in Schemes I, II, and III. Schemes II and III outline alternate synthesis of diastereomeric furanone intermediates. The Roman numerals following the names of the compounds refer to structures shown in Schemes I, II, and III. Those skilled in the art of organic synthesis will recognize that stereochemical directing groups other than (S)-(–)-4-benzyl-2-oxazolidinone (A) as shown in Scheme I, including, but not limited to, alternatively substituted oxazolidinones, ephedrine derivatives and chiral 2,10-camphorsultams may be used to obtain the same results. Also, hydroxyl and mercaptan protecting groups other than those used herein in the following specific examples can be utilized. Thiol protecting groups, W, which can be used include phenyl, —C(O)aryl where aryl is as defined and optionally substituted as above, —C(O)$C_1$–$C_{12}$ alkyl, —CR$^3$R$^4$R$^5$ where R$^3$, R$^4$ and R$^5$ are independently H, methyl, —OC$_1$–$C_{12}$alkyl, O-tetrahydropyranyl, —S-benzyl, and phenyl optionally substituted by methoxy, hydroxy, nitro, or methyl; disulfides or any other group suitable for protecting sulfur. Thiol protecting groups Z are H, phenyl, —CR$^3$R$^4$R$^5$ where R$^3$, R$^4$ and R$^5$ are independently H, methyl, —OC$_1$–$C_{12}$alkyl, O-tetrahydropyranyl, —S-benzyl, and phenyl optionally substituted by methoxy, hydroxy, nitro, or methyl; disulfides or any other group suitable for protecting sulfur. Hydroxyl protecting groups Y, include trimethylsilyl, t-butyldimethylsilyl, triethylsilyl, i-propyldimethylsilyl, trityldimethylsilyl, t-butyldiphenylsilyl, methyldi-i-propylsilyl, methyldi-t-butylsilyl, tri-i-propylsilyl, triphenylsilyl, benzyl, benzyl optionally substituted with methoxy, nitro, halo, cyano; and substituted methyl and ethyl ethers including triphenylmethyl, methoxymethyl, methoxyethoxymethyl, tetrahydropyran and allyl. Still other suitable oxygen and sulfur protecting groups as described in "Protective Groups in Organic Synthesis" (2nd ed., T. W. Greene and P. G. M. Wuts, John Wiley & Sons, New York, N.Y., 1991) may be used. Additionally, it will be apparent to those skilled in the art of organic synthesis that removal of the various chiral auxiliaries and mercapto and hydroxyl protecting groups may require methods other than those used in Schemes I, II, and III. It is understood by those skilled in the art that the various functionalities present on the molecule must be consistent with the chemical transformations proposed. This will frequently necessitate judgment as to the order of synthetic steps, protecting groups and deprotecting conditions.

Invention compounds and intermediates where $R^1$ is optionally substituted can be prepared following the steps outlined in schemes I, II, and III and following the procedures given in the examples starting with an appropriately substituted carboxylic acid of the formula R$^1$CH$_2$COOH or acid halide or anhydride thereof. Such acids are either commercially available or can be prepared according to standard literature procedures. Obviously, depending on the functionality of the substituent, standard protecting group chemistry may be required.

The formula I compounds of this invention where $R^2$ is α-OH (R configuration) or β-OH (S configuration) are prepared individually according to the process disclosed herein as outlined in Scheme I, starting with a common chiral acid 2(R)-2-R$^1$-pent-4-enoic acid of formula i. These 2-substituted pent-4-enoic acids are prepared according to literature procedures or by the sequence of reactions shown in Scheme I and in the following examples 1–6.

A synthetic scheme for preparing the starting acids (i) is shown in Scheme I. (4S)-4-Benzyl-3-((2R)-2-R$^1$-pent-4-enoyl)oxazolidin-2-ones, B, are prepared by acylation of (S)-(–)-4-benzyl-2-oxazolidinone, A, with an alkanoic acid halide of the formula R$^1$CH$_2$C(O)-halogen or the acid anhydride thereof, where R$^1$ is $C_1$–$C_{12}$ alkyl as defined above. A variety of N-acyl oxazolidinones, A, are known in the literature, including alkyl-O—CH$_2$aryl and alkyl-aryl derivatives which have previously been used for the synthesis of MMP inhibitors (Tomczuk, B. E. et. al. *Bioorg. & Med. Chem. Lett.* 5, 343, 1995; Chapman, K. T., et. al. *Bioorg. & Med. Chem. Lett.* 6, 803, 1996). The acyl chain is then alkylated stereospecifically α to the carbonyl with an allylating agent such as allyl halide or triflate, preferably allyl bromide, and the resulting (4S)-4-benzyl-3-((2R)-2-R$^1$-pent-4-enoyl)oxazolidin-2-one is hydrolyzed with lithium hydroperoxide or other suitable aqueous base to give the (2R)-2-R$^1$-penten-4-oic acids (i).

Reaction of the acid (i) with iodine affords predominantly the dihydrofuranone of formula iib, whereas reaction of the dimethylamide of the acid i with iodine affords predominantly the dihydrofuranone of formula iia. Either of the iodomethyldihydrofuranones iia or iib is converted to a protected thiol (iiia or iiib) by reaction with the anion of HSW, when appropriate, where W is as defined above, preferably by the sodium, lithium or potassium salt of thiolacetic acid. S-acetyl thiomethyldihydrofuranone iiia or iiib (W=Ac) is then hydrolyzed and the thiol protected as a cleavable thiol ether -SZ to give iva or ivb, where Z is defined as H, phenyl, —CR$^3$R$^4$R$^5$ where R$^3$, R$^4$ and R$^5$ are independently H, methyl, —OC$_1$–C$_{12}$alkyl, O-tetrahydropyranyl, —S-benzyl, and phenyl optionally substituted by methoxy, hydroxy, nitro, or methyl; disulfides or any other group suitable for protecting sulfur. The preferred protecting group Z for iva and ivb is the triphenylmethyl group which is readily formed from the thiol and trityl chloride in trifluoroacteic acid and is resistant to chemical reactions that occur in subsequent process steps.

Hydrolysis of the dihydrofuranone iva or ivb produces the S-protected 4-hydroxy-5-mercaptopentanoic acid va or vb respectively. The hydroxy group of the pentanoic acid va or vb is protected by a group Y by formation of an ether where Y is defined as H, trimethylsilyl, t-butyldimethylsilyl, triethylsilyl, i-propyldimethylsilyl, trityldimethylsilyl, t-butyldiphenylsilyl, methyldi-i-propylsilyl, methyldi-t-butylsilyl, tri-i-propylsilyl, triphenylsilyl, benzyl, benzyl optionally substituted with methoxy, nitro, halogen or cyano, triphenylmethyl, methoxymethyl, methoxyethoxymethyl, tetrahydropyran and allyl. The preferred protecting group Y is the t-butyldimethylsilyl group.

A O,S-protected acid via or vib is coupled with 2(S)-t-butyl-N-methylglycine using standard amide coupling techniques to obtain the respective protected formula I compound viia or viib. Removal of the hydroxyl protecting group (Y) gives the S-protected formula I compound viiia or viiib respectively. Removal of the sulfur protecting group (Z) from viiia or viiib then gives a formula I compound where R$^2$ is β-OH (S configuration) or α-OH (R configuration) respectively. Either of the formula I compounds where R$^2$ is OH and R$^6$ is H and Z is a protecting group can be oxidized followed by removal of the protecting group to give a compound of formula I where R$^2$ and R$^6$ together form a carbonyl group.

Thioacetic acid ester iiia or iiib (W=Ac) is also available via the commercially available (R)-(−)- or (S)-(+)-dihydro-5-(hydroxymethyl)-2(3H)-furanone as shown in Scheme II. Thus, protection of the hydroxy group of the (S)-(+) enantiomer as the t-butyldimethylsilyl ether or any suitable bulky protecting group such as a trityl group, followed by deprotonation of the resulting lactone and alkylation of this anion with R$^1$X, where R$^1$ is as previously defined and X is a suitable leaving group such as halide or triflate, gives lactone x. Lactone x is also available via alkylation of a suitably substituted pseudoephedrine amide, or via the alkylation of an achiral amide enolate with an enantiomerically pure epoxide followed by acid-induced hydrolysis/equilibration (Myers, A. G., et. al. *J. Org. Chem.* 61, 2428, 1996). Subsequent deprotection of the alcohol provides 2(R)-2-R$^1$-5(S)-5-hydroxymethyldihydrofuran-2-one(xia). (Lewis, C. N. et. al. *JCS Chem. Commun.* 1786, 1987). This alcohol may be converted into lactone-thioacetate iiia via a Mitsunobu-type reaction (Volante, R. P. *Tetrahedron Letters,* 22, 3119, 1981) or by conversion of the alcohol into a suitable leaving group such as halide, triflate, mesylate or tosylate followed by displacement with thioacetic acid or other suitable protected thiol equivalent and base. Using the same methodology (R)-(−)-dihydro-5-(hydroxymethyl)-2(3H)-furanone can be converted into thioacetate-lactone iiib via hydroxy-lactone intermediate xib (Scheme II).

Also, both diastereomeric lactones iiia and iiib can be synthesized from the pentenoic acid i as shown in Scheme III. Asymmetric dihydroxylation of the acid using Sharpless methodology (Sharpless, K. B., et. al. *Chem. Rev.* 94, 2483, 1994) provides diol xii which then undergoes acid catalyzed lactonization to give either of lactone-alcohols xia or xib. The lactones are then converted into the corresponding thioacetate-lactones, iiia or iiib via the same methodology described above for the conversion of iia to iiia in Scheme II.

Scheme I

Preparation of Mercaptoketones and Alcohols

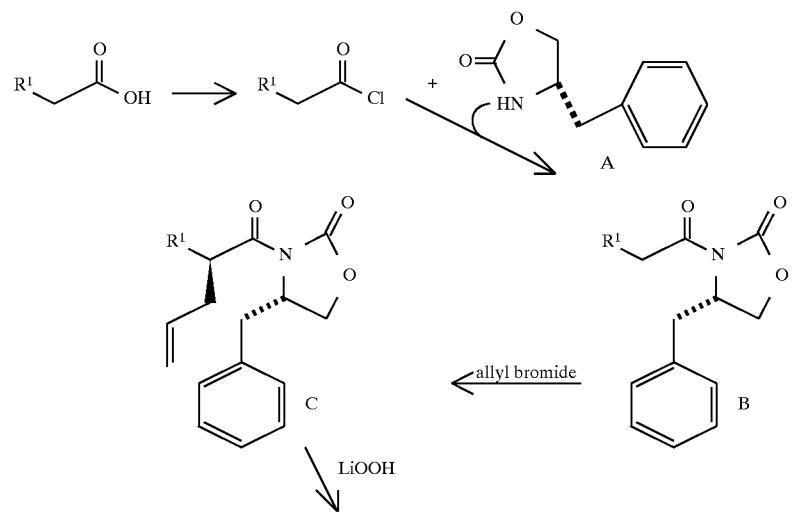

-continued
Scheme I
Preparation of Mercaptoketones and Alcohols
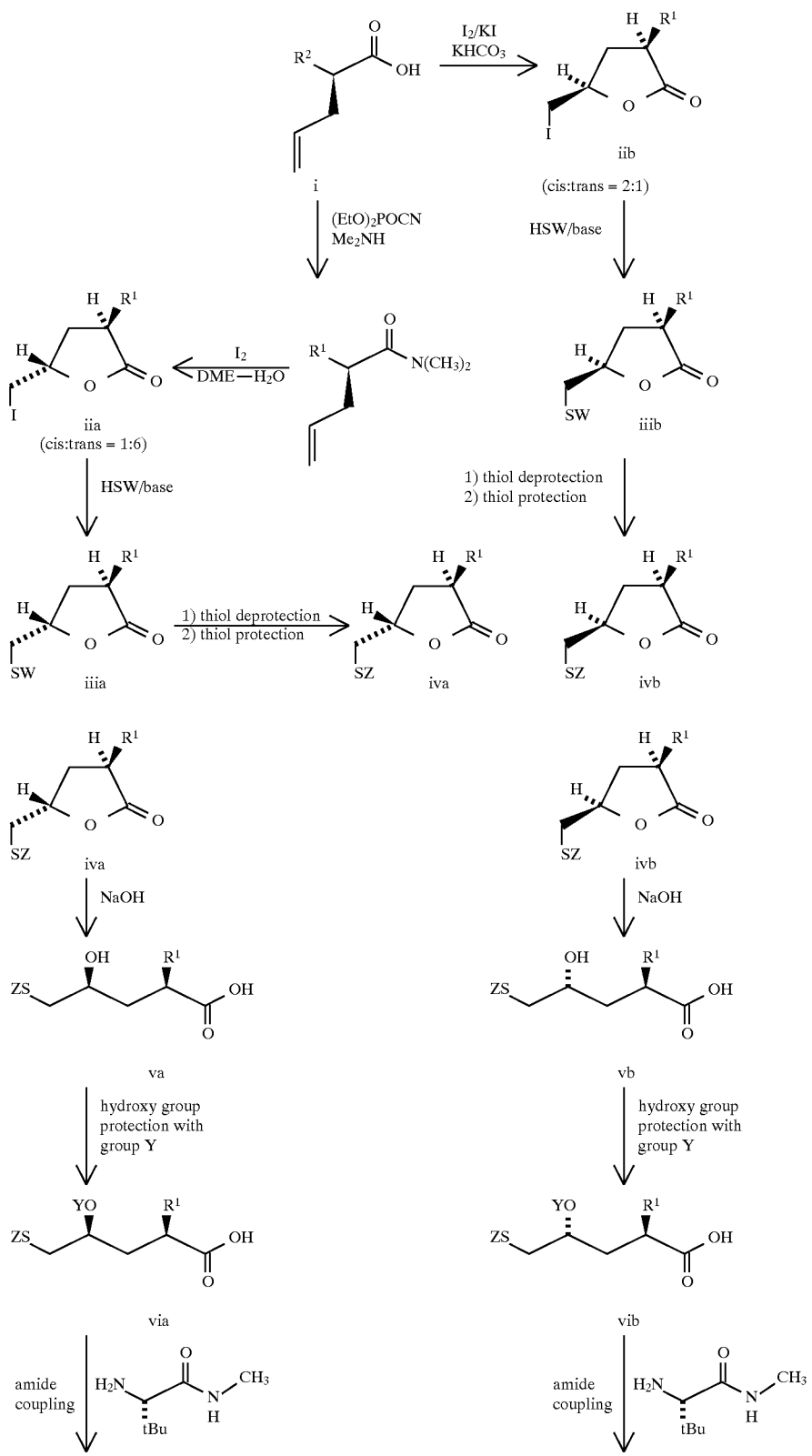

-continued
Scheme I
Preparation of Mercaptoketones and Alcohols

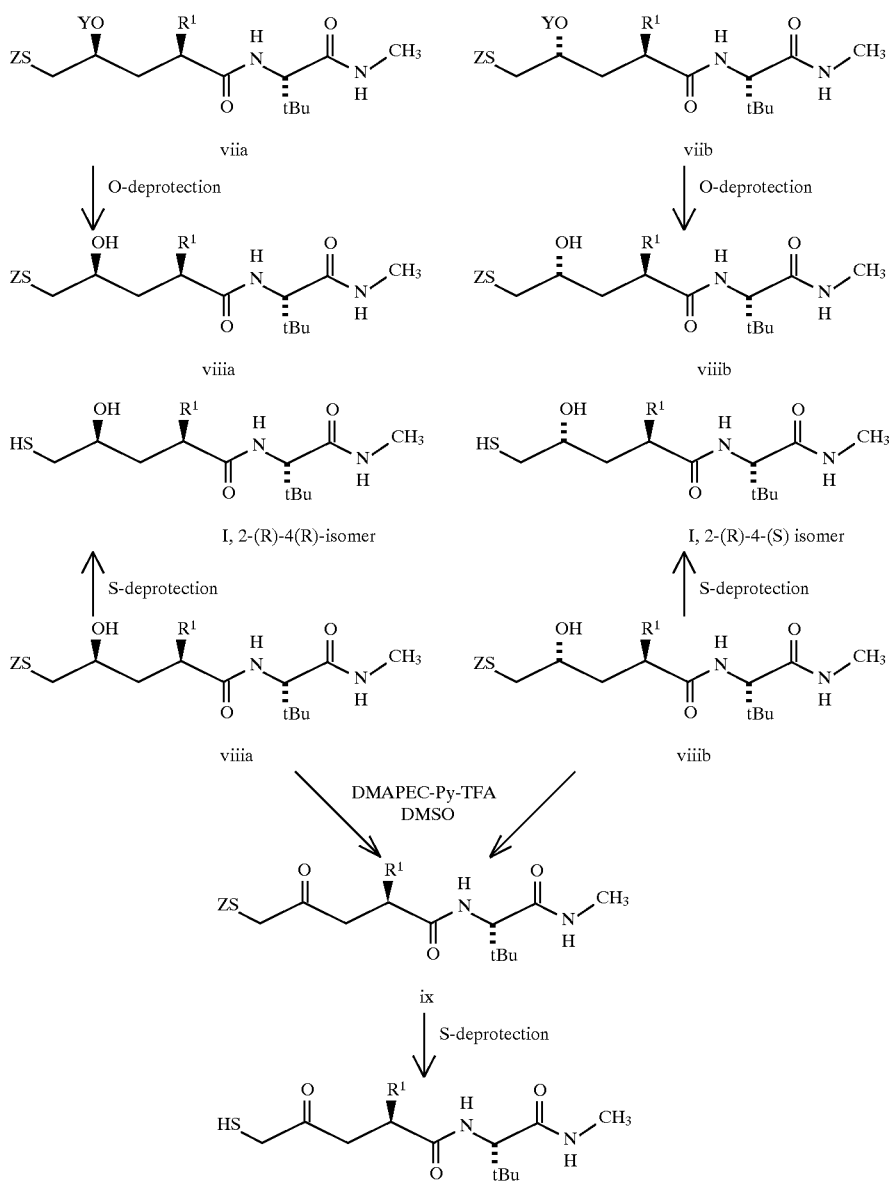

The following examples illustrate the process described above and are included for illustrative purposes only and are not to be construed as limiting to this invention in any way. The chemicals and reagents used in these procedures are either commercially available or readily prepared according to literature procedures by those skilled in the art of synthetic organic chemistry.

EXAMPLE 1

(S)-3-(1-Oxononanyl)-4-(phenylmethyl)-2-oxazolidinone

To a solution of 15.80 g (0.10 mol) of nonanoic acid in 150 mL of dichloromethane at 0° C. was added 0.1 mL of N,N-dimethylformamide and 9.59 mL (0.11 mol) of oxalyl chloride. The reaction mixture was allowed to warm to room temperature and stirred overnight. The reaction mixture was then concentrated in vacuo, diluted with hexanes and filtered. The filtrate was concentrated in vacuo to provide 17.67 g (100%) of nonanoyl chloride which was used without further purification in the next step.

To a solution of 25.2 g (0.142 mol) of (S)-(−)-4-benzyl-2-oxazolidinone (Aldrich Chemical Company) in 300 mL of THF cooled to −78° C. was added 97.0 mL (0.155 mol) of 1.6M n-butyllithium. The reaction mixture was stirred at −78° C. for 1 hour and nonanoyl chloride (17.4 g, 0.129 mol), dissolved in 75 mL of THF, was then added. The resulting mixture was stirred at −78° C. for 3 hours and then quenched with 5% HCl solution. The resulting mixture was extracted with ether and the combined organics were washed with water, saturated sodium bicarbonate and brine. The organics were then dried over $MgSO_4$, filtered and concentrated in vacuo. The residue was chromatographed on silica gel, eluting with ethyl acetate/hexanes (1:10), to provide 24.75 g (78%) of the desired product as a white solid.

EXAMPLE 2

(S)-3-(4-Methyl-1-oxopentyl)-4-(phenylmethyl)-2-oxazolidinone

Following the above procedure and substituting 15.0 g (0.129 mol) of 4-methylvaleric acid for the nonanoic acid, 23.69 g (66%) of the title compound is obtained.

EXAMPLE 3

(4S)-4-Benzyl-3-((2R)-2-heptyl-pent-4-enoyl)oxazolidin-2-one

To a solution of 5.50 g (0.017 mol) of the oxazolidinone in 40 mL of THF, cooled to −78° C., was added 17.3 mL (0.035 mol) of a 2.0M solution of lithium diisopropylamide in heptane/THF/benzene. The resulting mixture was stirred at −78° C. for 1 h and then neat allyl bromide (7.5 mL, 0.087 mol) was added to the reaction mixture. The reaction was allowed to warm to 0 degrees (ice bath) and stirred for an additional 3 h and then quenched with 5% HCl solution. The resulting mixture was extracted with ether and the combined organic layers were washed with water and brine, dried over $MgSO_4$, filtered and concentrated in vacuo. The residue was chromatographed on silica gel eluting with ethyl acetate/hexanes (1:10) to provide 5.0 g (81%) of the desired allylated product as a colorless oil. Electrospray Mass Spec: 358.2 $(M+H)^+$.

EXAMPLE 4

(4S)-4-Benzyl-3-((2R)-2-isobutyl-pent-4-enoyl)oxazolidin-2-one

In the same manner as described in Example 3 allylation of the isobutyl substituted oxazolidinone proceeded in 85% yield to provide the product as a colorless oil. CI Mass Spec: 316.3 (M+H).

EXAMPLE 5

(2R)-2-Heptyl-pent-4-enoic acid

To a solution of 8.69 g (0.024 mol) of the product from Example 3 in 425 mL of THF/H2O (3:1), cooled to 0 degrees, was added 10.8 mL (0.097 mol) of 30% hydrogen peroxide solution followed by 2.03 g (0.049 mol) of LiOH—$H_2O$. The resulting solution was stirred at 0° C. for 1.5 h and then quenched with a solution of 15.4 g of sodium sulfite in 100 mL of $H_2O$. The reaction mixture was then acidified to pH 3 with aqueous HCl and extracted with EtOAc. The combined organic layers were washed with water and brine, dried over $MgSO_4$, filtered and concentrated in vacuo. The residue was chromatographed on silica gel eluting with ethyl acetate/hexanes (1:10) to provide 4.33 g (90%) of the desired product as a colorless oil. CI Mass Spec: 199 (M+H).

EXAMPLE 6

(R)-2-Isobutyl-pent-4-enoic acid

In the same manner as described in Example 5 hydrolysis of the product of Example 4 proceeded in 92% yield to provide the product as a colorless oil. CI Mass Spec: 157.2 (M+H).

EXAMPLE 7

(R)-2-Heptyl-pent-4-enoic acid dimethylamide

To a mixture of 5.00 g (0.025 mol) of the product of Example 5 and 2.27 g (0.028 mol) of dimethylamine hydrochloride in DMF at 0° C. was added 4.21 mL (0.028 mol) of diethyl cyanophosphonate followed by 7.38 mL (0.053 mol) of triethylamine. The reaction mixture was stirred at 0 degrees for 1 h and then at room temperature for 3 h. The resulting pale yellow suspension was diluted with 750 mL of EtOAc/Hex (2:1) and this solution was then washed with 5% aqueous HCl solution, water, saturated sodium bicarbonate and brine. The organic layer was dried over magnesium sulfate, filtered and concentrated in vacuo. The residue was chromatographed on silica gel eluting with ethyl acetate/hexanes (1:4) to provide 5.68 g (100%) of the title compound as a colorless oil. CI Mass Spec: 226.3 (M+H).

EXAMPLE 8

(R)-2-Isobutyl-pent-4-enoic acid dimethylamide

In the same manner as described in Example 7 the product of Example 6 gave an 88% yield of the corresponding N,N-dimethyl amide as a colorless oil. CI Mass Spec: 184.2 (M+H).

EXAMPLE 9

(3R,5S)-3-Heptyl-5-iodomethyl-dihydrofuran-2-one

To a mixture of 5.68 g (0.025 mol) of the product of Example 7 in 90 mL of DME/$H_2O$ (1:1) at room temperature was added 7.69 g (0.030 mol) of iodine. The resulting solution was stirred at room temperature for 60 h and then diluted with ether and washed successively with a saturated aqueous solution of $Na_2S_2O_3$, saturated sodium bicarbonate solution and brine. The organic layer was dried over magnesium sulfate, filtered and concentrated in vacuo. The residue was chromatographed on silica gel eluting with ethyl acetate/hexanes (1:10) to provide 5.11 g (63%) of the title compound as a white solid and 0.788 g (10%) of the iodo-cis lactone as a colorless oil. CI Mass Spec: 325.3 (M+H).

EXAMPLE 10

(3R,5S)-5-Iodomethyl-3-isobutyl-dihydrofuran-2-one

In the same manner as described in Example 9 4.14 g (0.023 mol) of the product of Example 8 gave 4.539 g (71%) of the title compound as a colorless oil along with 0.691 g (11%) of the corresponding iodo-cis lactone. CI Mass Spec: 283.2 (M+H).

EXAMPLE 11

(3R,5R)-3-Heptyl-5-iodomethyl-dihydrofuran-2-one

To a solution of 7.14 g (0.036 mol) of the product of Example 5 in 750 mL of THF/$H_2O$ (2:1), cooled to 0 degrees, was added 7.22 g (0.072 mol) of $KHCO_3$ followed by 11.97 g (0.072 mol) of KI and then 18.30 g (0.072 mol) of iodine. The reaction was allowed to warm to room temperature and stirred for 18 h. The resulting mixture was diluted with ether and the organic layer was washed with aqueous sodium bisulfite solution, $H_2O$ and brine, dried over $MgSO_4$, filtered and concentrated in vacuo. The residue was chromatographed on silica gel eluting with ethyl acetate/hexanes (1:10) to provide 8.30 g (71%) of the title compound and 3.36 g (29%) of the corresponding iodo-trans lactone as white solids. CI Mass Spec: 325.3 (M+H).

EXAMPLE 12

(3R,5R)-5-Iodomethyl-3-isobutyl-dihydrofuran-2-one

In the same manner as described in Example 11 iodolactonization of 6.29 g (0.04 mol) of the product of Example 4 proceeded to provide 7.21 g (63%) of the title compound and 3.77 g (33%) of the corresponding iodo-trans lactone as colorless oils. CI Mass Spec: 283.2 (M+H).

EXAMPLE 13

Thioacetic acid S-((2R,4R)-4-heptyl-5-oxo-tetrahydrofuran-2-ylmethyl)ester

To a solution of 6.49 g (0.020 mol) of the product of Example 11 in 50mL of dry methanol was added 1.19 g (0.022 mol) of sodium methoxide followed by 5.73mL (0.080 mol) of thiolacetic acid. The resulting mixture was heated at reflux for 4.5 h and then cooled to room temperature and acidified with 5% HCl solution. The resulting solution was extracted with ether and the combined organic layers were washed with water and brine, dried over $MgSO_4$, filtered and concentrated in vacuo. The residue was chromatographed on silica gel eluting with ethyl acetate/hexanes (1:10) to provide 5.08 g (93%) of colorless oil. CI Mass Spec: 273.3 (M+H).

EXAMPLE 14

Thioacetic acid S-((2S,4R)-4-heptyl-5-oxo-tetrahydrofuran-2-ylmethyl)ester

In the same manner as described in Example 13 the product of Example 9 was converted into the corresponding thioacetate, obtained as a colorless oil in 82% yield. CI Mass Spec: 273.3 (M+H).

EXAMPLE 15

Thioacetic acid S-((4S,2R)-4-heptyl-5-oxo-tetrahydrofuran-2-ylmethyl)ester

In the same manner as described in Example 13 the product of Example 12 was converted into the corresponding thioacetate, obtained as a colorless oil in 75% yield. CI Mass Spec: 231.3 (M+H).

EXAMPLE 16

Thioacetic acid S-((2S,4R)-4-isobutyl-5-oxo-tetrahydrofuran-2-ylmethyl)ester

In the same manner as described in Example 13 the product of Example 10 was converted into the corresponding thioacetate, obtained as a colorless oil in 75% yield. CI Mass Spec: 231.3 (M+H).

EXAMPLE 17

(3R,5R)-3-Heptyl-5-tritylsulfanylmethyl-dihydrofuran-2-one

To a solution of the product of Example 13 in 100 mL of methanol, cooled to 0° C., was added 2.69 g (0.071 mol) of solid sodium borohydride in portions over 15 minutes. The reaction was then concentrated in vacuo, acidified with 10% HCl solution and extracted with methylene chloride. The combined organic layers were washed with water and brine, dried over $MgSO_4$, filtered and concentrated in vacuo. The resulting crude thiol was dissolved in 50 mL of trifluoroacetic acid and 5.98 g (0.023 mol) of trityl alcohol was added. After stirring at room temperature for 1 h the reaction mixture was concentrated in vacuo and the residue was chromatographed on silica gel eluting with ethyl acetate/hexanes (1:50) to provide 5.26 g (61%) of the desired product as a colorless oil. CI Mass Spec: 473.5 (M+H).

EXAMPLE 18

(3R,5S)-3-Heptyl-5-tritylsulfanylmethyl-dihydrofuran-2-one

In the same manner as described in Example 17 the product of Example 14 was converted into the corresponding S-trityl derivative, obtained as a colorless oil in 65% yield. CI Mass Spec: 473.5 (M+H).

EXAMPLE 19

(3R,5R)-3-Isobutyl-5-tritylsulfanylmethyl-dihydrofuran-2-one

In the same manner as described in Example 17 the product of Example 15 was converted into the corresponding S-trityl derivative, obtained as a colorless oil in 64% yield. CI Mass Spec: 431.4 (M+H).

EXAMPLE 20

(3R,5S)-3-Isobutyl-5-tritylsulfanylmethyl-dihydrofuran-2-one

In the same manner as described in Example 17 the product of Example 16 was converted into the corresponding S-trityl derivative, obtained as a colorless oil in 61% yield. CI Mass Spec: 431.5 (M+H).

EXAMPLE 21

(2R)-2-((2R)-2-Hydroxy-3-tritylsulfanylpropyl) nonanoic acid

To a solution of 3.72 g (7.88mmol) of the product of Example 17 in 100 mL of methanol/THF (1:1) at room temperature was added 16.7mL of 1.0N NaOH solution. The reaction was stirred at room temperature for 1 h and then diluted with 100 mL of $H_2O$ and carefully acidified to pH 6 with 5% HCl solution. The resulting mixture was extracted with EtOAc and the combined organic layers were washed with water and brine, dried over $MgSO_4$, filtered and concentrated in vacuo. The residue, 3.72 g (100%) of the crude hydroxy-acid was used in the next step (Example 25) without further purification. Electrospray Mass Spec: 489.4 (M–H)⁻.

EXAMPLE 22

(2R)-2-((2S)-2-Hydroxy-3-tritylsulfanylpropyl) nonanoic acid

In the same manner as described in Example 21 the product of Example 18 was converted into the corresponding hydroxy-acid derivative, obtained as a colorless oil in 95% yield. Electrospray Mass Spec: 489.4 (M–H)⁻.

EXAMPLE 23

(2R,4R)-4-Hydroxy-2-isobutyl-5-tritylsulfanylpentanoic acid

In the same manner as described in Example 21 the product of Example 19 was converted into the corresponding hydroxy-acid derivative, obtained as a colorless oil in 99% yield. Electrospray Mass Spec: 447.3 (M–H)⁻.

EXAMPLE 24

(2R,4S)-4-Hydroxy-2-isobutyl-5-tritylsulfanylpentanoic acid

In the same manner as described in Example 21 the product of Example 20 was converted into the corresponding hydroxy-acid derivative, obtained as a colorless oil in 99% yield. Electrospray Mass Spec: 447.3 (M−H)−.

EXAMPLE 25

(2R)-2-[(2R)-2-(tert-Butyl-dimethylsilanyloxy)-3-tritylsulfanylpropyl]nonanoic acid To a solution of 3.72 g (7.88 mmol) of the crude product of Example 21 dissolved in 10 mL of DMF was added 2.68 g (0.039 mol) of imidazole followed by 2.85 g (0.019 mol) of t-butyldimethylsilyl chloride. The reaction mixture was stirred at room temperature for 2 h and then poured into 200 mL of $H_2O$. The resulting solution was extracted with ether and the combined organic layers were washed with water and brine, dried over $MgSO_4$, filtered and concentrated in vacuo. The residue was dissolved in 10 mL of methanol/THF (1:1) and 5.0 mL of 1N NaOH solution was added. After stirring for 0.75 h at room temperature the reaction mixture was acidified with 5% HCl solution to pH 5 and then extracted with ether. The combined organic layers were washed with water and brine, dried over $MgSO_4$, filtered and concentrated in vacuo. The residue was chromatographed on silica gel eluting with ethyl acetate/hexanes (1:10) to provide 4.76 g (100%) of the desired product as a colorless oil. Electrospray Mass Spec: 603.5 (M−H)−.

EXAMPLE 26

(2R)-2-[(2S)-2-(tert-Butyl-dimethylsilanyloxy)-3-tritylsulfanylpropyl]nonanoic acid In the same manner as described in Example 25 the product of Example 22 was converted into the corresponding TBDMS ether-acid derivative, obtained as a colorless oil in 83% yield. Electrospray Mass Spec: 603.5 (M−H)−.

EXAMPLE 27

(2R,4S)-4-(tert-Butyldimethylsilanyloxy)-2-isobutyl-5-tritylsulfanylpentanoic acid In the same manner as described in Example 25 the product of Example 24 was converted into the corresponding TBDMS ether-acid derivative, obtained as a colorless oil in 91% yield. Electrospray Mass Spec: 561.4 (M−H)−.

EXAMPLE 28

(2R,4R)-4-(tert-Butyldimethylsilanyloxy)-2-isobutyl-5-tritylsulfanylpentanoic acid In the same manner as described in Example 25 the product of Example 23 was converted into the corresponding TBDMS ether-acid derivative, obtained as a colorless oil in 95% yield. Electrospray Mass Spec: 561.4 (M−H)−.

EXAMPLE 29

(2R)-2-[(2R)-2-(tert-Butyl-dimethylsilanyloxy)-3-tritylsulfanylpropyl]-nonanoic acid ((1S)-2,2-dimethyl-1-methylcarbamylprophyl amide To a solution of 4.76 g (7.88 mmol) of the product of Example 25 dissolved in 150 mL of dichloromethane was added 1.42 g (9.85 mmol) of t-butyl glycine-N-methylamide followed by 1.86 mL (0.013 mmol) of triethylamine and 1.67 mL (0.011 mmol) of diethylcyanophosphonate. The reaction mixture was stirred at room temperature for 12 h and then concentrated in vacuo. The resulting residue was diluted with ether and the organics were washed with 5% HCl solution, water and brine. The organic layer was then dried over $MgSO_4$, filtered and concentrated in vacuo to provide 5.13 g (89%) of the desired product as an oil pure enough for use in the next step. FAB Mass Spec: 753.4 (M+Na).

EXAMPLE 30

(2R)-2-[(2S)-2-(tert-Butyl-dimethylsilanyloxy)-3-tritylsulfanylpropyl]-nonanoic acid ((1S)-2,2-dimethyl-1-methylcarbonylpropyl)amide Using the same procedure described in Example 29 6.80 g (11.26 mmol) of the product of Example 26 produced 7.71 g (94%) of the desired product as a colorless oil. FAB Mass Spec: 753.4 (M+Na).

EXAMPLE 31

(2R,4R)-4-(tertButyldimethylsilanyloxy) -2-isobutyl-5-tritylsulfanylpentanoic acid ((1S)-2,2-dimethyl-1-methylcarbamoylpropyl)amide Using the same procedure described in Example 29 5.81 g (10.33 mmol) of the product of Example 28 produced 4.62 g (65%) of the desired product as a colorless oil. $^1$H NMR (300 MHz, $CDCl_3$) δ7.44 (m, 5H), 7.26 (m, 10H), 6.16 (m, 1H), 5.96 (d, J=9 Hz, 1H), 4.19 (d, J=9 Hz, 1H), 3.58 (m, 1H), 2.76 (d, J=4.7 Hz, 3H), 2.29 (dd, J=6.2,12 Hz, 1H), 2.13 (dd, J=4.5,12 Hz, 1H), 2.0 (m, 1H), 1.7–1.1 (m, 3H), 0.92 (s, 9H), 0.85 (s, 9H), 0.82 (dd, J=6,10 Hz), −0.039 (s, 3H), −0.078 (s, 3H).

EXAMPLE 32

(2R,4S)-4-(tertButyldimethylsilanyloxy)-2-isobutyl-5-tritylsulfanylpentanoic acid (1S)-2,2-dimethyl-1-methylcarbamoylpropyl)amide Using the same procedure described in Example 29 7.20 g (12.81 mmol) of the product of Example 27 produced 5.53 g (63%) of the desired product as a colorless oil. Electrospray Mass Spec: 711.4 (M+Na)+.

EXAMPLE 33

(2R)-2-((2R)-2-Hydroxy-3-tritylsulfanylpropyl) nonanoic acid ((1S)-2,2-dimethyl-1-methylcarbamoylpropyl)amide To a solution of 5.13 g (7.027 mmol) of the product of Example 29 dissolved in 75 mL of THF was added 17.6 mL (0.018 mmol) of a 1.0M solution of tetrabutylammonium fluoride in THF. The reaction mixture was stirred at room temperature for 4 h and then diluted with ether. The resulting solution was washed with water and brine, dried over $MgSO_4$, filtered and concentrated in vacuo. The residue was chromatographed on silica gel eluting with EtOAc/Hexanes (gradient: 1:3–1:1) to provide 2.78 g (64%) of the desired product as a colorless oil. Electrospray Mass Spec: 617.5 (M+H)+.

EXAMPLE 34

(2R) -2-((2S)-2-Hyd roxy-3-tritylsulfanyl propyl) nonanoic acid ((1S)-2,2-dimethyl-1-methylcarbamoylpropyl)amide Using the same procedure described in Example 33 7.63 g (0.126 mmol) of the product of Example 30 produced 4.22 g (66%) of the desired product as a colorless oil. Electrospray Mass Spec: 617.5 (M+H)+.

EXAMPLE 35

(2R,4R)-4-Hydroxy-2-isobutyl-5-tritylsulfanylpentanoic acid ((1S)-2,2-dimethyl-1-methylcarbamoylpropyl)amide Using the same procedure described in Example 33 4.58 g (0.126 mmol) of the product of Example 31 produced 3.66 g (96%) of the desired product as a colorless oil. Electrospray Mass Spec: 575.4 (M+H)+.

EXAMPLE 36

(2R,4S)-4-Hydroxy-2-isobutyl-5-tritylsulfanylpentanoic acid ((1S)-2,2-dimethyl-1-methylcarbamoylpropyl)amide Using the same procedure described in Example 31 5.50 g (0.126 mmol) of the product of Example 30 produced 3.87 g (84%) of the desired product as a colorless oil. Electrospray Mass Spec: 575.3 (M+H)+.

EXAMPLE 37

(2R)-2-((2R)-2-Hydroxy-3-mercaptopropyl)nonanoic acid ((1S)-2,2-dimethyl-1-methylcarbamoylpropyl)amide To a solution of 0.700 g (1.136 mmol) of the product of Example 33 and 0.363 mL (2.273 mmol) of triethylsilane dissolved in 10 mL of dichloromethane was dropwise added 10 mL of trifluoroacetic acid. The reaction mixture was stirred at room temperature for 0.5 h and then concentrated in vacuo. The residue was chromatographed on silica gel eluting with EtOAc/Hexanes (gradient: 1:3–1:1) to provide 0.263 g (62%) of the desired product as a colorless oil. Electrospray Mass Spec: 375.4 (M+H)+.

EXAMPLE 38

(2R)-2-((2S)-2-Hydroxy-3-mercaptopropyl)nonanoic acid ((1S)-2,2-dimethyl-l-methylcarbamoylpropyl)amide Using the same procedure described in Example 37 1.0 g (1.62 mmol) of the product of Example 34 produced 0.24 g (40%) of the desired product as a colorless oil. Electrospray Mass Spec: 375.4 (M+H)+.

EXAMPLE 39

(2R,4R)-4-Hydroxy-2-isobutyl-5-mercaptopentanoic acid ((1S)-2,2-dimethyl-1-methylcarbamoylpropyl)amide Using the same procedure described in Example 37 1.50 g (2.61 mmol) of the product of Example 35 produced 0.47 g (54%) of the desired product as a colorless oil. Electrospray Mass Spec: 333.3 (M+H)+.

EXAMPLE 40

(2R,4S)-4-Hydroxy-2-isobutyl-5-mercaptopentanoic acid ((1S)-2,2-dimethyl-1-methylcarbamoylpropyl)amide Using the same procedure described in Example 37 1.50 g (2.61 mmol) of the product of Example 36 produced 0.14 g (16%) of the desired product as a colorless oil. Electrospray Mass Spec: 333.3 (M+H)+.

EXAMPLE 41

(2R)-2-(2-Oxo-3-tritylsulfanylpropyl)nonanoic acid ((1S)-2,2-dimethyl-1-methylcarbamoylpropyl)amide To a solution of 0.962 g (1.562 mmol) of the product of Example 33 in 3mL of DMSO was added 0.505 mL (6.246 mmol) of pyridine followed by 0.120 mL (1.562 mmol) of trifluoroacetic acid and 0.898 (4.685 mmol) of 1-(3-dimethylaminopropyl)-3-ethylcarbodiimide hydrochloride. The reaction mixture was stirred at room temperature for 36 h and then diluted with 200 mL of EtOAc. The resulting solution was washed with 0.1N HCl solution, water, saturated NaHCO$_3$ solution and brine, dried over MgSO$_4$, filtered and concentrated in vacuo. The residue, 0.948 g (99%) was used in the next step without purification. Electrospray Mass Spec: 615.4 (M+H)+.

EXAMPLE 42

(2R)-2-Isobutyl-4-oxo-5-tritylsulfanylpentanoic acid ((1S)-2,2-dimethyl-1-methylcarbamoylpropyl)amide Using the same procedure described in Example 41 1.25 g (2.18 mmol) of the product of Example 35 produced 1.25 g (100%) of the desired product as a colorless oil. Electrospray Mass Spec: 573.4 (M+H)+.

EXAMPLE 43

(2R)-2-(3-Mercapto-2-oxopropyl)nonanoic acid ((1S)-2,2-dimethyl-1-methylcarbamoylpropyl)amide Using the same procedure described in Example 37 1.985 g (3.23 mmol) of the product of Example 41 produced 0.506 g (42%) of the desired product as a colorless oil. Electrospray Mass Spec: 373.4 (M+H)+.

EXAMPLE 44

(2R)-2-Isobutyl-5-mercapto-4-oxopentanoic acid ((1S)-2,2-dimethyl-1-methylcarbamoylpropyl)amide Using the same procedure described in Example 37 2.49 g (4.35 mmol) of the product of Example 42 produced 0.462 g (32%) of the desired product as a colorless oil. Electrospray Mass Spec: 331.3 (M+H)+.

Pharmacology

Table 1 summarizes the pharmacological data obtained for the four diastereomeric alcohols and two mercaptoketones of this invention where R is isobutyl or heptyl. The pharmacological procedures follow the table. The data show that the 2(S) hydroxy diastereomers have superior and unexpected potency over the 2(R) hydroxy analogs both in vivo and in vitro, the latter being less potent than the keto compounds.

TABLE 1

In vitro and In vivo Inhibition of Matrix Metalloproteinases

| Example | R' | $R^2$ and $R^6$ | $R^1$ Collagenase $IC_{50}$ (nM) or % inhibition | Stromelysin $IC_{50}$ (nM) or % inhibition | Gelatinase $IC_{50}$ (nM) | in vivo % Collangenase I inhibition |
|---|---|---|---|---|---|---|
| 43 | =O | heptyl | 30.0 | 28 | | 0.73/50 mpk* |
| 44 | =O | isobutyl | 38.0 | 58% @ 1 μM | | 4.8/60 mpk |
| 38 | 2(S) OH | heptyl | 30.0 | 96% @ 0.1 μM | | 22.2/50 mpk |
| 40 | 2(S) OH | isobutyl | 41.0 | 51% @ 1 μM | 19 | 84.8/50 mpk |
| 35 | 2(R) OH | heptyl | 72% @ 1 μM | 38% @ 1 μM | | 0.44/50 mpk |
| 39 | 2(R) OH | isobutyl | 228 | 6% @ 300 nM | 106 | 20.4/50 mpk |

*mpk = milligrams/kilogram

Stromelysin Inhibition in vitro.

The assay is based on the cleavage of the thiopeptide substrate ((Ac-Pro-Leu-Gly(2-mercapto-4-methylpentanoyl)Leu-Gly-OEt), Bachem Bioscience) by the enzyme stromelysin, releasing the substrate product which forms a colorimetric reaction with DTNB ((5,5'-dithiobis(2-nitrobenzoic acid)). The thiopeptide substrate is made up as a 20 mM stock in 100% DMSO and stored frozen while the DTNB stock is dissolved in 100% DMSO and stored as a 100 mM stock at room temperature. Both the substrate and DTNB are diluted to 1 mM with assay buffer (50 mM HEPES, pH 7.0, 5 mM $CaCl_2$) before use. The stock of human recombinant stromelysin (truncated, Affymax) is diluted with assay buffer to a final concentration of 12.5 nM in the reaction.

The enzyme, DTNB, and substrate (10 μM final concentration) with/without inhibitor (total reaction volume of 200 μL) is added to a 96 well plate and then the increase in color is monitored spectrophotometrically for 5 minutes at 405 nanometers (nm) on a plate reader. The increase in $OD_{405}$ is plotted and the slope of the line is calculated which represents the reaction rate.

The linearity of the reaction rate is confirmed ($r^2>0.85$). The mean of the control rate is calculated and compared for statistical significance ($p<0.05$) with drug-treated rates using Dunnett's multiple comparison test. Dose-response relationships can be generated using multiple doses of drug and $IC_{50}$ values with 95% CI are estimated using linear regression (IPRED, HTB) (Weingarten and Feder, Spectrophometric Assay For Vertebrate Collagenase, Anal. Biochem 147, 437–440 (1985)).

Gelatinase Inhibition in vitro.

The assay is based on the cleavage of the thiopeptide substrate ((Ac-Pro-Leu-Gly(2-mercapto-4-methylpentanoyl)Leu-Gly-OEt), Bachem Bioscience) by the enzyme gelatinase, releasing the substrate product which forms a colorimetric reaction with DTNB ((5,5'-dithiobis(2-nitrobenzoic acid)). The thiopeptide substrate is made up fresh as a 20 mM stock in 100% DMSO and the DTNB is dissolved in 100% DMSO and stored in dark as a 100 mM stock at room temperature. Both the substrate and DTNB are diluted to 1 mM with assay buffer (50 mM HEPES, pH 7.0, 5 mM $CaCl_2$, 0.2% Brij) before use. The stock of human neutrophil gelatinase B is diluted with assay buffer to a final concentration of 0.15 nM.

The assay buffer, enzyme, DTNB, and substrate (500 μM final concentration) with/without inhibitor (total reaction volume of 200 μL) is added to a 96 well plate and then the increase in color is monitored spectrophotometrically for 5 minutes at 405 nanometers (nm) on a plate reader. The increase in $OD_{405}$ is plotted and the slope of the line is calculated which represents the reaction rate.

The linearity of the reaction rate is confirmed ($r^2>0.85$). The mean of the control rate is calculated and compared for statistical significance ($p<0.05$) with drug-treated rates using Dunnett's multiple comparison test. Dose-response relationships can be generated using multiple doses of drug and $IC_{50}$ values with 95% CI are estimated using linear regression (IPRED, HTB). (Weingarten and Feder, Spectrophometric Assay For Vertebrate Collagenase, Anal. Biochem 147, 437–440 (1985)).

Collagenase Inhibition in vitro

The assay is based on the cleavage of a peptide substrate ((Dnp-Pro-Cha-Gly-Cys(Me)-His-Ala-Lys(NMa)-$NH_2$), Peptide International, Inc.) by collagenase releasing the fluorescent NMa group which is quantitated on the fluorometer. Dnp quenches the NMa fluorescence in the intact substrate. The assay is run in HCBC assay buffer (50 mM HEPES, pH 7.0, 5 mM $Ca^{+2}$, 0.02% Brij, 0.5% cysteine), with human recombinant fibroblast collagenase (truncated, mw 18,828, WAR, Radnor). Substrate is dissolved in methanol and stored frozen in 1 mM aliquots. Collagenase is stored frozen in buffer in 25 μM aliquots. For the assay, substrate is dissolved in HCBC buffer to a final concentration of 10 μM and collagenase to a final concentration of 5 nM. Compounds are dissolved in methanol, DMSO, or HCBC. The methanol and DMSO are diluted in HCBC to <1%. Compounds are added to the 96 well plate containing enzyme and the reaction is started by the addition of substrate.

The reaction is read (excitation 340 nm, emission 444 nm) for 10 minutes and the increase in fluorescence over time is plotted as a linear line. The slope of the line is calculated and represents the reaction rate.

The linearity of the reaction rate is confirmed ($r^2>0.85$). The mean of the control rate is calculated and compared for statistical significance ($p<0.05$) with drug-treated rates using Dunnett's multiple comparison test. Dose-response relationships can be generated using multiple doses of drug and $IC_{50}$ values with 95% CI are estimated using linear regression (IPRED, HTB) (Bickett, D. M. et al., A High Throughput Fluorogenic Substrate For Interstitial Collagenase (MMP-1) and Gelatinase (MMP-9), Anal. Biochem. 212, 58–64 (1993)).

In vivo MMP Inhibition

A 2 cm piece of dialysis tubing (molecular weight cut-off 12–14,000, 10 mm flat width) containing matrix metalloproteinase enzyme (stromelysin, collagenase or gelatinase in 0.5 mL of buffer) is implanted either ip or sc (in the back) of a rat (Sprague-Dawley, 150–200 g) or mouse (CD-1, 25–50 g) under anesthesia. Drugs are administered PO, IP, SC or IV through a canula in the jugular vein. Drugs are administered in a dose volume of 0.1 to 0.25 mL/animal. Contents of the dialysis tubing is collected and enzyme activity assayed.

Enzyme reaction rates for each dialysis tube are calculated. Tubes from at least 3 different animals are used to calculate the mean±sem. Statistical significance (p<0.05) of vehicle-treated animals versus drug-treated animals is determined by analysis of variance. (*Agents and Actions* 21: 331, 1987)

Pharmaceutical Composition

Compounds of this invention may be administered neat or with a pharmaceutical carrier to a patient in need thereof. The pharmaceutical carrier may be solid or liquid.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties n suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such a solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferable sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

The dosage to be used in inhibiting the matrix metalloproteinases in a patient must be subjectively determined by the attending physician. The variables involved include the severity of the dysfunction, and the size, age, and response pattern of the patient. Treatment will generally be initiated with small dosages less than the optimum dose of the compound. Thereafter the dosage is increased until the optimum effect under the circumstances is reached. Precise dosages will be determined by the administering physician based on experience with the individual subject treated and standard medical principles.

Preferably the pharmaceutical composition is in unit dosage form, e.g., as tablets or capsules. In such form, the composition is sub-divided in unit dose containing appropriate quantities of the active ingredient; the unit dosage form can be packaged compositions, for example packed powders, vials, ampoules, prefilled syringes or sachets containing liquids. The unit dosage form can be, for example, a capsule or tablet itself, or it can be the appropriate number of any such compositions in package form.

What is claimed is:

1. A process for the preparation of a diastereomerically and enantiomerically pure compound according to the formula

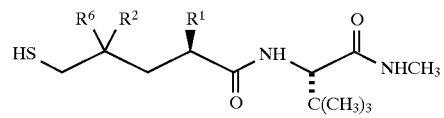

where $R^1$ is $C_1$–$C_{12}$ alkyl, straight or branched and optionally substituted by halogen, hydroxy, $C_1$–$C_6$ alkoxy, amino, carboxyl, $C_1$–$C_6$ alkoxycarbonyl, carboxamido, nitrile, mono- or di-($C_1$–$C_6$)alkylamino, thio, $C_1$–$C_6$ alkylthio, aryl, —Oaryl or —OCH$_2$aryl where aryl is optionally substituted with $C_1$–C6 alkyl, $C_1$–$C_6$ alkoxy, carboxy, halogen, cyano, nitro, carboxamido, or hydroxy; and $C_1$–$C_6$ alkanesulfonyloxy where aryl is a 5 to 10 membered carbocyclic or heterocyclic mono or bicyclic aromatic group selected from the benzene, furan, thiophene, imidazole, naphthalene, quinoline, indole, benzothiophene, benzimidazole, pyridine, pyrimidine, and benzofuran; $R^2$ is (S)—OH and $R^6$ is H, which comprises:

(1) reacting a (3R,5S)-5-iodomethyl-3-$R^1$-dihydrofuran-2-one with the anion of HSW, where W is defined as phenyl, —C(O)aryl and —C(O)-substituted aryl where aryl is a 5 to 10 membered carbocyclic or heterocyclic mono or bicyclic aromatic group selected from the benzene, furan, thiophene, imidazole, naphthalene, quinoline, indole, benzothiophene, benzimidazole, pyridine, pyrimidine, and benzofuran, optionally substituted with $C_1$–$C_6$ alkyl, $C_1$–$C_6$ alkoxy, carboxy, halogen, cyano, nitro, carboxamido, or hydroxy; —C(O)—$C_1$–$C_{12}$alkyl and —CR$^3$R$^4$R$^5$ where R$^3$, R$^4$, and R$^5$ are independently selected from H, methyl, —O—-$C_1$–$C_{12}$alkyl, O-tetrahydrophyranyl, —S-benzyl and phenyl optionally substituted with methoxy, hydroxy, nitro, or methyl, to provide lactone iiia, (2) deprotection of the sulfur of lactone iiia of step (1) under reducing conditions, acid hydrolysis or base hydrolysis to provide compound iva (Z=H), (3) protection of the free thiol of step (2) above to provide compound iva where Z is H, phenyl, —CR$^3$R$^4$R$^5$ where R$^3$, R$^4$ and R$^5$ are independently H, methyl, —O—$C_1$–$C_{12}$alkyl, O-tetrahydropyranyl, —S-benzyl, phenyl optionally substituted with methoxy, hydroxy, nitro, or methyl; disulfides or any other group suitable for protecting sulfur, (4) hydrolysis of the furanone of step (3) with aqueous acid or base to give compound va, a thiol-protected (2R)-2-$R^1$-(4R)-4-hydroxy-5-mercaptopentanoic acid, where Z is as defined above, (5) protection of the hydroxy group of compound va of step (4) with a protecting group Y to give compound via where Y is selected from trimethylsilyl, tert-butyldimethylsilyl, triethylsilyl, isopropyldimethylsilyl, trityldimethylsilyl, tert-butyldiphenylsilyl, methyldiisopropylsilyl, methyldi-tert-butylsilyl, triisopropylsilyl, triphenylsilyl, benzyl optionally substituted with methoxy, nitro, halogen or cyano; substituted methyl or ethyl ethers including triphenylmethyl, methoxymethyl, methoxyethoxymethyl, tetrahydropyranyl, or allyl, (6) amidation of carboxylic acid via of step (5) with (2S)-t-butylglycine N-methylamide and a peptide coupling reagent, to provide compound viia where Y and Z are as defined above, (7) removal of the protecting group Y from the hydroxyl group of compound viia of step (6) to provide alcohol viiia, where Z is as defined above, (8) removal of the thiol protecting group of compound viiia of step (7) to provide a compound of the above formula.

2. The process according to claim 1 for the preparation of a diastereomerically and enantiomerically pure compound according to the formula

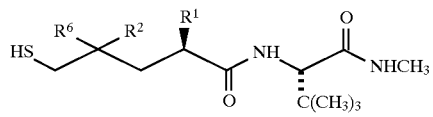

where $R^1$ is $C_1$–$C_{12}$ alkyl, straight or branched and optionally substituted by halogen, hydroxy, $C_1$–$C_6$ alkoxy, amino, carboxyl, $C_1$–$C_6$ alkoxycarbonyl, carboxamido, nitrile, mono- or di-($C_1$–$C_6$)alkylamino, thio, $C_1$–$C_6$ alkylthio, aryl, —Oaryl or —OCH$_2$aryl where aryl is optionally substituted with $C_1$–$C_6$ alkyl, $C_1$–$C_6$ alkoxy, carboxy, halogen, cyano, nitro, carboxamido, or hydroxy; and $C_1$–$C_6$ alkanesulfonyloxy where aryl is a 5 to 10 membered carbocyclic or heterocyclic mono or bicyclic aromatic group selected from the benzene, furan, thiophene, imidazole, naphthalene, quinoline, indole, benzothiophene, benzimidazole, pyridine, pyrimidine, and benzofuran; $R^2$ is (S)—OH and $R^6$ is H, which comprises:

(1) reacting a (3R,5S)-5-iodomethyl-3-$R^1$-dihydrofuran-2-one with the sodium, lithium or potassium salt of thiolacetic acid, to provide lactone iiia where W is acetyl, (2) deprotection of the sulfur of lactone iiia of step (1) wherein the acetyl group is removed by treatment with sodium borohydride in methanol or ethanol to provide compound iva (Z=H), (3) protection of the free thiol of step (2) above to provide compound iva where Z is triphenylmethyl, (4) hydrolysis of the furanone of step (3) with aqueous acid or base, preferably sodium hydroxide, to give compound va, a thiol-protected (2R)-2-$R^1$-(4R)-4-hydroxy-5-mercaptopentanoic acid, where Z is triphenylmethyl, (5) protection of the hydroxy group of compound va of step (4) with the t-butyldimethylsilyl protecting group to give compound via where Y t-butyldimethylsilyl, (6) amidation of carboxylic acid via of step (5) with (2S)-t-butylglycine N methylamide and the peptide coupling reagent diethylcyanophosphonate, and triethylamine, to provide compound viia where Y is t-butyldimethylsilyl and Z is triphenylmethyl, (7) removal of the t-butyldimethylsilyl protecting group Y from the hydroxyl group of compound viia of step (6) with tetrabutylammonium fluoride to provide alcohol viiia, where Z is triphenylmethyl, (8) removal of the triphenylmethyl thiol protecting group of compound viiia of step (7) with trifluoroacetic acid and triethylsilane to provide a compound of the above formula.

3. A process for the preparation of a compound according to the formula

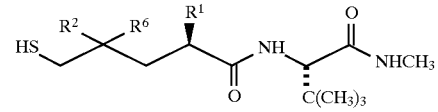

where $R^1$ is $C_1$–$C_{12}$ alkyl, straight or branched and optionally substituted by halogen, hydroxy, $C_1$–$C_6$ alkoxy, amino, carboxyl, $C_1$–$C_6$ alkoxycarbonyl, carboxamido, nitrile, mono- or di-($C_1$–$C_6$)alkylamino, thio, $C_1$–$C_6$ alkylthio, aryl, —Oaryl or —OCH$_2$aryl where aryl is optionally substituted with $C_1$–$C_6$ alkyl, $C_1$–$C_6$ alkoxy, carboxy, halogen, cyano, nitro, carboxamido, or hydroxy; and $C_1$–$C_6$ alkanesulfonyloxy where aryl is a 5 to 10 membered carbocyclic or heterocyclic mono or bicyclic aromatic group selected from the benzene, furan, thiophene, imidazole, naphthalene, quinoline, indole, benzothiophene, benzimidazole, pyridine, pyrimidine, and benzofuran; $R^2$ is (R)—OH and $R^6$ is H which comprises:

(1) reacting a (3R,5R)-5-iodomethyl-3-$R^1$-dihydrofuran-2-one with the anion of HSW, where W is defined as phenyl, —C(O)aryl and —C(O)-substituted aryl where aryl is a 5 to 10 membered carbocyclic or heterocyclic mono or bicyclic aromatic group selected from the benzene, furan, thiophene, imidazole, naphthalene, quinoline, indole, benzothiophene, benzimidazole, pyridine, pyrimidine, and benzofuran, optionally substituted with $C_1$–$C_6$ alkyl, $C_1$–$C_6$ alkoxy, carboxy, halogen, cyano, nitro, carboxamido, or hydroxy; —C(O)—$C_1$–$C_{12}$alkyl and —CR$^3$R$^4$R$^5$ where R$^3$, R$^4$, and R$^5$ are independently selected from H, methyl, —O—$C_1$–$C_{12}$alkyl, O-tetrahydropyranyl, —S-benzyl and phenyl optionally substituted with methoxy, hydroxy, nitro, or methyl, to provide lactone iiib, (2) deprotection of the sulfur of lactone iiib of step (1) under reducing conditions, acid hydrolysis or base hydrolysis to provide compound ivb (Z=H), (3) protection of the free thiol of step (2) above to provide compound ivb where Z is H, phenyl, —CR$^3$R$^4$R$^5$ where R$^3$, R$^4$ and R$^5$ are independently H, methyl, —O—$C_1$–$C_{12}$alkyl, O-tetrahydropyranyl, —S-benzyl, phenyl optionally substituted with methoxy, hydroxy, nitro, or methyl; disulfides or any other group suitable for protecting sulfur, (4) hydrolysis of the furanone of step (3) with aqueous acid or base to give compound vb, a thiol-protected (2R)-2-$R^1$-(4R)-4-hydroxy-5-mercaptopentanoic acid, where Z is as defined above, (5) protection of the hydroxy group of compound vb of step (4) with a protecting group Y to give compound vib where Y is selected from trimethylsilyl, tert-butyldimethylsilyl, triethylsilyl, isopropyldimethylsilyl, trityldimethylsilyl, tert-butyldiphenylsilyl, methyldiisopropylsilyl, methylditert-butylsilyl, triisopropylsilyl, triphenylsilyl, benzyl optionally substituted with methoxy, nitro, halogen or cyano; substituted methyl or ethyl ethers including triphenylmethyl, methoxymethyl, methoxyethoxymethyl, tetrahydropyranyl, or allyl, (6) amidation of carboxylic acid vib of step (5) with (2S)-t-butylglycine N-methylamide and a peptide coupling reagent, to provide compound viib where Y and Z are as defined above, (7) removal of the protecting group Y from the hydroxyl group of compound viib of step (6) to provide alcohol viiib, where Z is as defined above, (8) removal of the thiol protecting group of compound viiib of step (7) to provide a compound of the above formula.

4. The process according to claim 3 for the preparation of a diastereomerically and enantiomerically pure compound according to the formula

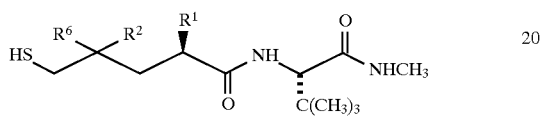

where $R^1$ is $C_1$–$C_{12}$ alkyl, straight or branched and optionally substituted by halogen, hydroxy, $C_1$–$C_6$ alkoxy, amino, carboxyl, $C_1$–C6 alkoxycarbonyl, carboxamido, nitrile, mono- or di-($C_1$–$C_6$)alkylamino, thio, $C_1$–$C_6$ alkylthio, aryl, —Oaryl or —OCH$_2$aryl where aryl is optionally substituted with $C_1$–$C_6$ alkyl, $C_1$–$C_6$ alkoxy, carboxy, halogen, cyano, nitro, carboxamido, or hydroxy; and $C_1$–$C_6$ alkanesulfonyloxy where aryl is a 5 to 10 membered carbocyclic or heterocyclic mono or bicyclic aromatic group selected from the benzene, furan, thiophene, imidazole, naphthalene, quinoline, indole, benzothiophene, benzimidazole, pyridine, pyrimidine, and benzofuran; $R^2$ is (R)—OH and $R^6$ is H, which comprises:

(1) reacting a (3R,5R)-5-iodomethyl-3-$R^1$-dihydrofuran-2-one with the sodium, lithium or potassium salt of thiolacetic acid, to provide lactone iiib where W is acetyl, (2) deprotection of the sulfur of lactone iiib of step (1) wherein the acetyl group is removed by treatment with sodium borohydride in methanol or ethanol to provide compound ivb (Z=H), (3) protection of the free thiol of step (2) above to provide compound ivb where Z is triphenylmethyl, (4) hydrolysis of the furanone of step (3) with aqueous acid or base, preferably sodium hydroxide, to give compound vb, a thiol-protected (2R)-2-$R^1$-(4R)-4-hydroxy-5-mercaptopentanoic acid, where Z is triphenylmethyl, (5) protection of the hydroxy group of compound vb of step (4) with the t-butyldimethylsilyl protecting group to give compound vib where Y t-butyldimethylsilyl, (6) amidation of carboxylic acid vib of step (5) with (2S)-t-butylglycine N-methylamide and the peptide coupling reagent diethylcyanophosphonate, and triethylamine, to provide compound viib where Y is t-butyldimethylsilyl and Z is triphenylmethyl, (7) removal of the t-butyldimethylsilyl protecting group Y from the hydroxyl group of compound viib of step (6) with tetrabutylammonium fluoride to provide alcohol viiib, where Z is triphenylmethyl, (8) removal of the triphenylmethyl thiol protecting group of compound viiib of step (7) with trifluoroacetic acid and triethylsilane to provide a compound of the above ormula.

* * * * *